United States Patent [19]
Tomita et al.

[11] Patent Number: 5,814,280
[45] Date of Patent: Sep. 29, 1998

[54] SEMICONDUCTOR PH SENSOR AND CIRCUIT AND METHOD OF MAKING SAME

[75] Inventors: Katsuhiko Tomita; Tsuyoshi Nakanishi; Syuji Takamatsu; Satoshi Nomura; Hiroki Tanabe, all of Miyanohigashi-machi, Japan

[73] Assignee: Horiba, Ltd, Kyoto, Japan

[21] Appl. No.: 752,580

[22] Filed: Nov. 21, 1996

[30] Foreign Application Priority Data

Nov. 24, 1995 [JP] Japan ................................ 7-329836
Oct. 11, 1996 [JP] Japan ................................ 8-289370

[51] Int. Cl.$^6$ .................................................. G01N 21/00
[52] U.S. Cl. ................................ 422/82.01; 422/82.02; 422/82.03; 422/82.04
[58] Field of Search .................... 422/82.01, 82.02, 422/82.03, 82.04

[56] References Cited

U.S. PATENT DOCUMENTS 4,505,799  3/1985  Baxter ................................ 204/416
5,068,205  11/1991  Baxter et al. ........................ 437/205

*Primary Examiner*—Edward J. Cain
*Attorney, Agent, or Firm*—Price, Gess & Ubell

[57] ABSTRACT

A pH sensor having an ISFET is provided on a crystalline substrate of silicon with a thin film of aluminum oxide formed to have epitaxial growth with an overlaying thin film of silicon epitaxial grown on the aluminum oxide layer. A source element and a drain element are provided on the silicon film, and a pH responsive film layer is connected to the source and drain. The pH sensor can be accompanied with appropriate circuitry also integrally formed on the same epitaxial SOI substrate.

19 Claims, 3 Drawing Sheets

SEMICONDUCTOR PH SENSOR AND CIRCUIT AND METHOD OF MAKING SAME

BACKGROUND OF THE INVENTION

1. Field of the Invention

The present invention relates to a pH sensor and, more specifically, to a semiconductor pH sensor formed on a substrate with appropriate circuitry for amplifying and processing a pH signal and method of making the same.

2. Description of Related Art pH sensors have been formed as an ion-sensitive field effect transistor (ISFET) in the prior art. The conventional ISFET has utilized a process wherein an ISFET is formed in an upper surface of a silicon substrate with a subsequent cutting of the silicon substrate to form individual ISFET sensor. Because the silicon substrate is cut and the surface is exposed, it has been necessary in the prior art to seal the exposed surface with resin and the like to secure sufficient insulation. However, the resulting reliability of the pH sensor has been lowered. Additionally, in order to provide sufficient insulative properties, the manufacturing process must become complicated and therefore it becomes difficult to obtain a low-priced pH sensor, or a one-chip pH sensor.

One possible solution could be to form an ISFET on the upper surface of a silicon-on-sapphire (SOS) substrate. However, an SOS substrate is relatively expensive and can cost several times that of the ordinary silicon, single-crystal substrate. Thus, there is a desire in the prior art to provide an improved pH sensor with additional features and capabilities, which can be economically manufactured through an efficient method.

OBJECTS AND SUMMARY OF THE INVENTION

The present invention provides an improved pH sensor, which can be economically and simply manufactured, while maintaining good and stabilized electric insulation properties with high performance. The present invention accomplishes these advantages with a pH sensor provided on a unitary chip.

The pH sensor of an ion-sensitive field effect transistor includes a crystalline substrate of silicon with a thin film of aluminum oxide deposited on the substrate in such a manner to encourage epitaxial growth. Subsequently, a thin film of silicon is epitaxially grown on the aluminum oxide layer and oxidized through thermal oxidation to provide a silicon oxide film layer of 0.1 $\mu$m. The oxidation step can be performed by a wet oxidation process of applying oxygen gas and steam at 1000° C. for a time period of about 70 minutes. The silicon layer is approximately 1 $\mu$m in thickness, while the aluminum oxide film layer is approximately 0.1 $\mu$m in thickness.

Predetermined areas of the silicon oxide film are etched with a buffered fluorine solution to form a location for a source element and a drain element. A thermal diffusion of the appropriate impurities, such as boron or phosphorus, into the etched portions can be accomplished with a subsequent removal of the oxidized silicon layer between the source element and the drain element. Subsequently, an oxide film is formed over the source element, the drain element, and the silicon film between the source element and the drain element. The oxidation step can be performed by a dry oxidation process of applying oxygen gas at 1000° C. for a time period of about 100 minutes. Finally, a pH responsive film, such as $Si_3N_e$ is formed over the oxide film to a thickness of 0.1 $\mu$m.

An appropriate amplifying and processing circuit can be also formed directly on the same substrate of silicon immediately adjacent to and electrically connected with the pH sensor to provide amplification along with a comparative electrode and a temperature sensor with a temperature correcting diode.

Thus, the pH sensor of the present invention uses an ISFET sensor formed on an epitaxial grown substrate having a structure comprising silicon/aluminum oxide/silicon (Si/$\gamma$-Al$_2$O$_3$/Si), hereinafter called epitaxial SOI (silicon-on-insulator) substrate. This pH sensor is formed by a process of subjecting an aluminum oxide thin film to epitaxial growth on a silicon single-crystal substrate and subjecting a silicon thin film to epitaxial growth on the aluminum oxide thin film. The pH sensor can be formed on a single-chip substrate with not only the ISFET, but further supplement IC circuits for carrying out signal processing, such as amplification and comparison on the same epitaxial growth SOI substrate. Additionally, the one-chip pH sensor may be connected to a one-chip microcomputer for further processing of the pH signal.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a semiconductor pH sensor and circuit and method of making the same.

Figure 1:
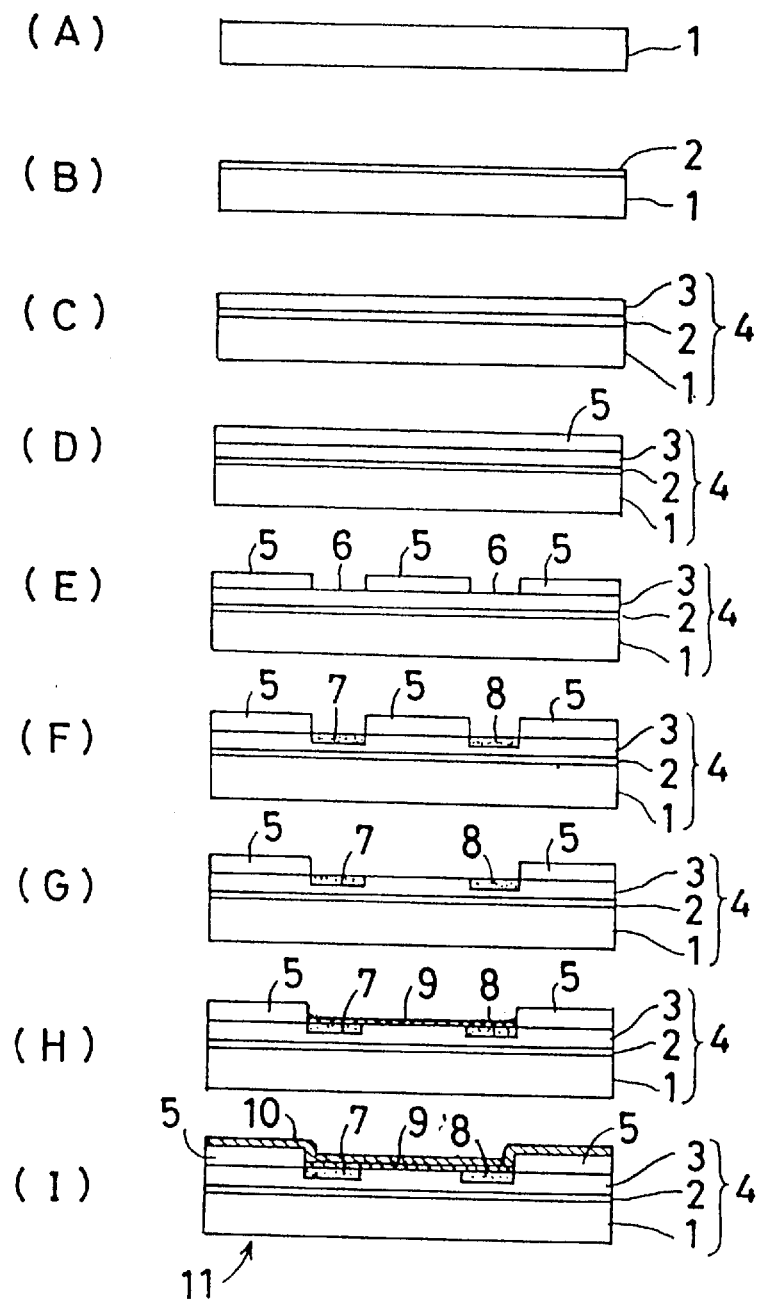
FIGS. 1A through 1I are schematic cross-sectional views to show the manufacturing process of the pH sensor of the present invention.

Referring to FIG. 1A through 1I schematic cross-sectional views of the pH sensor of the present invention are disclosed and an illustration of the manufacturing method and process of forming a pH sensor with an ISFET on a substrate is illustrated. Thus, in FIG. 1A, a silicon single-crystal substrate 1 having a thickness of about 500 $\mu$m is disclosed. The upper surface of the silicon single-crystal substrate 1 can be subject to a depositing, for example, by a chemical vapor deposition procedure (CVD) of an aluminum oxide thin film having an epitaxial growth across the substrate surface whereby an aluminum oxide thin film 2, $\gamma$-AL$_2$O$_3$ is formed to a thickness of about 0.1 $\mu$m. Subsequently, as shown in FIG. 1C a silicon thin film 3 can also be deposited by a CVD process across the upper surface of the aluminum oxide thin film 2 to form a silicon thin film 3 having a thickness of about 1 μm. The appropriate temperature and environmental conditions for depositing these films to encourage an epitaxial growth are known and will not be repeated here. Thus, by these procedures there is formed an epitaxial SOI substrate 4 having a structure comprising a silicon single-crystal substrate 1, aluminum oxide thin film 2, and a silicon thin film 3. At this point in the procedure, a thermal oxidation can occur, for example, in a wet oxidation step of bleeding oxygen and steam at the appropriate temperature range of about 1000° C. for about a time period of 70 minutes, so that on the upper surface of the silicon thin film 3, an oxide film $SIO_2$ is formed having a thickness of about 0.5 μm.

An appropriate mask to define regions to establish, for example, a source and a drain, for example, with a photoresist material, can be provided. While not shown, it should be appreciated that supplementary circuit patterns can also be provided for the remaining portions of the substrate so that an integral combination pH sensor and supporting circuit, e.g., amplification, comparison, etc., can be provided on a unitary chip.

The oxide film, disclosed in FIG. 1D is then appropriately etched with a buffered fluorine solution of fluorine and ammonium fluoride, as shown in FIG. 1E to remove a portion of the oxide film 5 and to leave windows or exposed surfaces in the oxide film, as shown in the areas 6.

As known in the industry, a thermal diffusion technique can be employed to add impurities into the silicon thin film 3 to form a source element 7 and a drain element 8 on the exposed silicon thin film, as shown in FIG. 1F. Both source element 7 and drain element 8 are made from the same material, but if the substrate 1 is of n-type silicon, boron (B) is used, while if the substrate 1 is of p-type silicon, phosphorus (P) is used. In general, since p-type silicon is used for substrate 1, source element 7 and drain element 8 are formed with phosphorus.

By again providing a thermal oxidation step, for example, in a dry oxidation step of bleeding in oxygen at the appropriate temperature range of about 1000° C. for about a time period of 100 minutes, an oxide film is formed (gate oxidation) on the surfaces of the silicon thin film 3, the source element 7, and the drain element 8, as shown in FIG. 1H. The thickness of this oxide film can be approximately 0.1 μm. Finally, a pH-sensitive membrane or responsive film 10 of $Si_3N_4$ of about 0.1 μm in thickness can be provided on the upper surface, again by a CVD process so that an ISFET 11 is formed to provide the pH sensor on the epitaxial SOI substrate 4, as shown in FIG. 1(I).

Thus, a pH sensor 11 can be easily manufactured in the method steps described above to provide a semiconductor substrate having an epitaxial SOI substrate 4 with the structure of a silicon thin film 3 wherein γ-$AL_2O_3$ is subject to epitaxial growth on the upper surface of the silicon single-crystal substrate 1 to form an aluminum oxide thin film 2 and further an SI single-crystal, subject to epitaxial growth on the surface of the aluminum oxide film 2. As a result, a pH sensor having good and stabilized electric insulating properties is provided.

Figure 2:
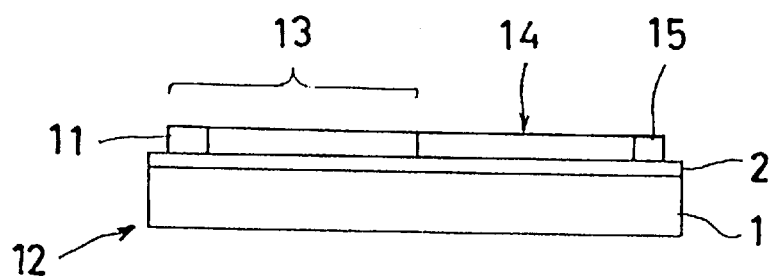
FIG. 2 is a schematic cross-sectional view showing the construction of a one-chip pH sensor of the present invention.

Referring to FIG. 2, a schematic cross-sectional illustration is disclosed of a unitary pH sensor with supporting circuitry is disclosed as element 12. Thus, by assembling an ISFET 11 along with an IC circuit 14, a sensor portion 13 can be provided on the surface of the unitary substrate 1 and over an underlying aluminum oxide thin film 2. The IC circuit 14 is capable of treating the output signal from the sensor part 13 and can be an MOS integrated circuit made in the manufacturing process of the ISFET 11. As shown in FIG. 2, the element 12 can be an interface connector for providing connection with external devices, such as LEDs and displays. Alternatively, a microchip with a microprocessor can also be connected so that a two-part chip set can be provided for utilization of the pH sensor. Thus, providing a one-chip pH sensor unit 12 and including the sensor portion 13, including the ISFET 11, and IC circuitry 14 on the same structure of an epitaxial SOI substrate 4, insulation can be easily obtained and an excellent resulting product that can be used as a chemical sensor that is relatively resistant to contact with the solutions to be measured, can be achieved. This durable product is of particular use in both environmental and industrial measurements so that reliable, long-term readings can be generated.

Since it is possible to not only manufacture the pH sensor (ISFET) with a semiconductor process, but also to manufacture the electronic circuitry, including, for example, an amplifying circuit, there is considerable advantage in cost saving by providing a unitary manufacturing process.

One particular application of a one-chip pH sensor 12 having the above structure can be for use in a meter for monitoring service water, or to be provided in an apparatus for determining the pH of food stuff in an industrial environment. Many other applications having this chip set as an integral part of the sensor portion of an analytical instrument can be readily envisioned with an emphasis upon durability and low cost.

Figure 3:
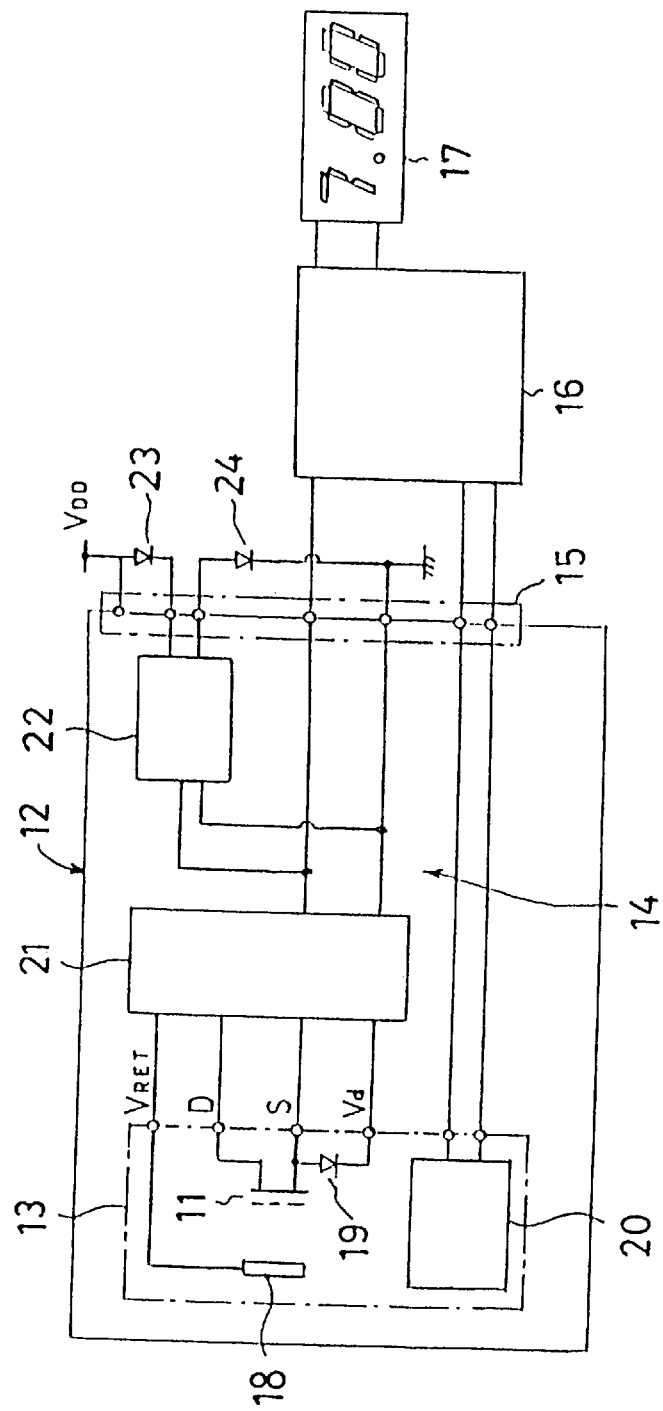
FIG. 3 is a schematic view showing an embodiment of the pH sensor of the present invention in combination with a microchip and display.

FIG. 3 is a schematic drawing to disclose one possible use of the one-chip pH sensor 12 of the present invention. In FIG. 3, a one-chip microcomputer 16 is electrically connected through an interface part 15 to the one-chip pH sensor 12. The microcomputer 16 can, for example, drive an LCD display with an appropriate power source (not shown). The sensor 13 can include a reference electrode 18 formed adjacent the above ISFET 11 and in addition, a temperature compensation diode 19, for example, Ag/AgCl, can be used to adjust the electrical characteristic of the ISFET 11 to make the measurements temperature insensitive. The temperature sensor 20 for temperature compensation of pH sensitivity is shown with lead lines connected to the microcomputer 16 to provide an appropriate temperature correction. For example, temperature conversion tables can be utilized or a conversion algorithm can be established, particularly if the temperature range is linear.

The IC circuit 14 comprises an amplifier 21 and a compensation circuit 22. As can be a light-emitting diode, such as a red light LED 23, can be utilized to glow when the pH is smaller than 7, while an LED 24 can be utilized in the blue range, when the pH is larger than 7, to thereby supplementing the numerical display 17.

As can be appreciated, considerable advantages can be achieved by integrating the sensor 13 and the IC circuit 14 on the same epitaxial SOI substrate 4. It is also possible for the sensor 13 and the IC circuit 14 to be provided on separate substrates, but the present invention realizes substantial economies by the integration on the same substrate. Advantageously, the sensor 13 is formed on the epitaxial growth SOI substrate 4, even if the IC circuit 14 is provided on a conventional silicon substrate.

In accordance with the present invention, the pH sensor having an ISFET is formed on an epitaxial SOI substrate with a structure comprising a silicon/aluminum oxide/silicon laminate formed by a process of subjecting an aluminum oxide thin firm to epitaxial growth on a silicon single-crystal substrate, and then subjecting a silicon thin film to the pH is smaller than 7, while an LED 24 can be utilized in the blue range, when the pH is larger than 7, to thereby supplementing the numerical display 17.

As can be appreciated, considerable advantages can be achieved by integrating the sensor 13 and the IC circuit 14 on the same epitaxial SOI substrate 4. It is also possible for the sensor 13 and the IC circuit 14 to be provided on separate substrates, but the present invention realizes substantial economies by the integration on the same substrate. Advantageously, the sensor 13 is formed on the epitaxial growth SOI substrate 4, even if the IC circuit 14 is provided on a conventional silicon substrate.

In accordance with the present invention, the pH sensor having an ISFET is formed on an epitaxial SOI substrate with a structure comprising a silicon/aluminum oxide/silicon laminate formed by a process of subjecting an aluminum oxide thin film to epitaxial growth on a silicon single-crystal substrate, and then subjecting a silicon thin film to epitaxial growth on the aluminum oxide thin film to thereby provide both good and stabilized electrical insulating properties with a high performance.

As can be realized, by providing only a one-chip pH sensor with the ISFET and the IC circuit for carrying out signal processes formed on the epitaxial SOI substrate, considerable advantages can be achieved in both economy, stabilized electrical insulation properties, and high performance. Thus, while it is possible for the one-chip pH sensor of the present invention to provide a sensor portion and an IC circuit portion that are separable so that the application range can be broad, the preferred embodiment combines the two for both durability, reliability, and low manufacturing cost.

What is claimed is:

1. A pH sensor of an ion-sensitive field-effect transistor comprising:
   a crystalline substrate of silicon;
   a thin film of aluminum oxide deposited on the substrate and having an epitaxial growth;
   a thin film of silicon epitaxially grown on the aluminum oxide layer;
   a source element provided on the thin silicon film;
   a drain element provided on the thin silicon film; and
   a pH responsive film layer connected to the source element and drain element.

2. The invention of claim 1 wherein the pH responsive film layer is $Si_3N_4$.

3. The invention of claim 1 further including an oxide film formed over the source element and the drain element.

4. The invention of claim 1 further including circuit means formed on the same substrate for processing a measured pH signal detected by the pH sensor.

5. The invention of claim 4 wherein the circuit means includes an amplifier.

6. The invention of claim 1 wherein the aluminum oxide film layer is approximately 0.1 μm in thickness.

7. The invention of claim 1 wherein the silicon layer is approximately 1 μm in thickness.

8. A semiconductor sensor unit for measuring and processing a pH signal comprising:
   a crystalline substrate of silicon;
   a thin film of aluminum oxide deposited on a sensor portion of the substrate;
   a thin film of silicon positioned over the aluminum oxide film;
   a source element provided on the silicon film;
   a drain element provided on the silicon film;
   a pH responsive film layer connected to the source element and drain element;
   a circuit pattern provided on the substrate adjacent to and connected with the sensor portion, including an amplifier for amplifying any pH signal generated in the sensor portion.

9. The invention of claim 8 wherein the pH responsive film layer is $Si_3N_4$.

10. The invention of claim 9 further including an oxide film formed over the source element and drain elements.

11. The invention of claim 8 further including a one-chip microcomputer connected to the circuit pattern for processing any pH signal.

12. A method of forming a pH sensor comprising:
    providing a crystalline substrate of silicon;
    depositing an aluminum oxide film to provide an epitaxial growth on the substrate;
    depositing a silicon film over the aluminum oxide film;
    oxidizing the silicon film to provide a silicon oxide film layer;
    etching a pair of separate portions of the silicon oxide film layer to form a source element and a drain element;
    diffusing impurities into the etched portions;
    removing the oxidized layer between the source element and the drain element forming an oxide film over the source element, drain element, and the silicon film between the source element and drain element; and
    forming a pH responsive film over the oxide film.

13. The method of claim 12, wherein the step of oxidizing the silicon film includes introducing oxygen and steam at 1000° C. for about 70 minutes.

14. The method of claim 13, wherein the step of forming an oxide film includes introducing oxygen at 1000° C. for about 100 minutes.

15. The method of claim 12, wherein the pH-responsive film is $Si_3N_4$.

16. The method of claim 12, wherein the etching is performed with a solution of fluorine and ammonium fluoride.

17. The invention of Claim 10 wherein the oxide film is $SiO_2$.

18. The invention of claim 2 wherein an oxide film of $SiO_2$ is formed over the source element and the drain element.

19. The invention of claim 4 wherein a microcomputer is connected to the circuit pattern for processing any pH signal.

* * * * *